United States Patent

Dejesus et al.

(10) Patent No.: US 7,540,981 B2
(45) Date of Patent: Jun. 2, 2009

(54) BIASABLE TRANSFER COMPOSITION AND MEMBER

(75) Inventors: M. Cristina B. Dejesus, Fairport, NY (US); John C. Wilson, Rochester, NY (US); Charles E. Hewitt, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 657 days.

(21) Appl. No.: 11/241,386

(22) Filed: Sep. 30, 2005

(65) Prior Publication Data

US 2007/0075298 A1    Apr. 5, 2007

(51) Int. Cl.
G03G 13/36 (2006.01)
G03G 13/00 (2006.01)
G03G 9/10 (2006.01)
H01B 1/12 (2006.01)
H01B 1/20 (2006.01)

(52) U.S. Cl. .......... 252/519.1; 252/500; 428/425.8; 428/423.1; 428/411.1; 430/62; 430/126.1; 430/126.2; 399/313; 399/159

(58) Field of Classification Search ........... 252/519.1, 252/500; 430/31, 36, 62, 126.1, 902; 428/425.8, 428/423.1; 399/159, 313; 562/84
See application file for complete search history.

(56) References Cited

U.S. PATENT DOCUMENTS

| | | | |
|---|---|---|---|
| 3,959,574 A | 5/1976 | Seanor et al. | |
| 4,265,045 A | 5/1981 | Garbini | |
| 4,496,643 A | 1/1985 | Wilson et al. | |
| 4,729,925 A * | 3/1988 | Chen et al. | 428/425.8 |
| 4,742,941 A | 5/1988 | Tastet | |
| 4,762,941 A * | 8/1988 | Chen et al. | 558/44 |
| 5,212,032 A * | 5/1993 | Wilson et al. | 430/65 |
| 5,571,457 A * | 11/1996 | Vreeland et al. | 252/519.21 |
| 5,733,695 A * | 3/1998 | Molaire et al. | 430/59.4 |
| 2007/0075295 A1 | 4/2007 | Dejesus et al. | |
| 2007/0075296 A1 | 4/2007 | DeJesus et al. | |
| 2007/0075297 A1 | 4/2007 | Dejesus et al. | |

FOREIGN PATENT DOCUMENTS

JP    05297703    * 11/1993

* cited by examiner

*Primary Examiner*—Stanley Silverman
*Assistant Examiner*—Kallambella Vijayakumar
(74) *Attorney, Agent, or Firm*—Carl F. Ruoff

(57) ABSTRACT

The present invention provides a polymeric material containing conductivity control agents derived from a hydroxyalkylphosphonium sulfonate salt. The conductivity control agents can be used with semi-conductive rolls, belts and other biasable members. The inclusion of the conductivity control agent in polymeric or polyurethane elastomers extends the electrical life of the polymer biasable member in low humidity environments. Additionally, the resistivity of the elastomeric polyurethane or polymer on the biasable member is controlled to a desirable value by adjusting the conductivity control agent level in the elastomers.

11 Claims, 1 Drawing Sheet

BIASABLE TRANSFER COMPOSITION AND MEMBER

CROSS-REFERENCE TO RELATED APPLICATIONS

Reference is made to the following co-pending, commonly assigned, U.S. patent applications Ser. Nos. 11/240,717, 11/240,825, 11/240,931.

FIELD OF THE INVENTION

This invention relates generally to the field of polymers and particularly to polymers that are electrically conductive having an improved or extended electrical life when in dry environments.

BACKGROUND OF THE INVENTION

The majority of conventional commodity polymers such as polyethylene, polystyrene and polyamide are inherently insulators due to their lack of intrinsic charge carriers. When it is required, the electrical conductivity of polymers can be increased by incorporating conductive additives such as carbon black and metal particles or conventional antistat agents.

The addition of conductive additives to polymers has expanded the application of these polymers to fields where it is desirable for the product to have some electrical conductivity. One example involves the use of electrically biasable polyurethane transfer rolls or webs, which are used in electrostatographic copying systems or apparati to transfer images from an electrostatographic element such as a photoconductor, to a final support material or receiver such as a web or sheet of paper.

The process of transferring toner material from the electrostatographic element or photoconductor to the receiving sheet or copy sheet, is realized at a transfer station. In a conventional transfer station, transfer is commonly achieved by applying electrostatic force fields in a transfer nip sufficient to overcome the forces that hold the toner particles to their original support surface on the photo-receptive member or photoconductor. These electrostatic force fields operate to attract and transfer the toner particles over and onto the copy sheet or other supporting second surface.

A biasable transfer member, such as a biasable transfer roll is used to control the forces acting on the toner during the transfer process enabling the toner to be transferred from the photoconductor to the final support material.

In order to achieve optimal image transfer, the resistivity of such materials have to be controlled to a critical range and, at the same time, the resistivity has to be relatively insensitive to moisture variations so that the resistivity of the materials remains relatively constant within the ranges required for optimal image transfer.

It has been found that the most favorable volume resistivity of the polyurethane transfer member should be between $1.0\times10^6$ and $5.0\times10^{11}$ ohm cm in order to optimize the toner image transfer from the surface of the photoconductor to the final support surface.

U.S. Pat. No. 3,959,574 describes elastomeric polyurethane transfer members such as rolls and belts having ionic additives to control the resistivity. The effectiveness of the additives for reducing the resistivity of the elastomers according to the patent is achieved if the additives are soluble or dispersible in the elastomeric polyurethane. However, over time, the ionic conductivity control additives migrate out depleting ions and increasing the resistivity of the polyurethane.

Chen et al, in U.S. Pat. Nos. 4,729,925 and 4,762,941 disclose a polyurethane elastomer in which certain polyol conductivity-control agents formed from certain salts complexed with particular polyester diols such as for example, bis[oxydiethylenebis(polycaprolactone)yl] 5-sulfo-1,3-benzenedicarboxylate, methyltriphenylphosphonium salt, are copolymerized with certain polyisocyanate prepolymers and other polyols normally used to make polyurethanes to yield elastomers with resistivity that can be maintained between $1.0\times10^9$ and $1.0\times10^{11}$ ohm cm. According to this patent, the conductivity control agent is an integral part of the polymer and therefore not subject to being leached out as described in the prior case in which the conductivity control agent is included as an additive. The polyurethane elastomers of this patent however, are still moisture sensitive. For example, curve 2 in FIG. 2 of U.S. Pat. No. 4,729,925, indicates that the volume resistivity of the conductive polyurethane elastomers of Example 15 decrease by a factor of about 6.5 when the relative humidity changed from 25% to about 85%.

Wilson et al, in U.S. Pat. No. 5,212,032, disclose, as coating materials for biasable transfer members, certain elastomeric polyurethanes containing, as conductivity control agents for controlling the resistivity of the elastomeric coating and hence that of the biasable transfer member to a range from about $1.0\times10^7$ to about $5.0\times10^{10}$ ohm cm, certain ionizable ferric halides selected from the group consisting of ferric fluoride, ferric chloride and ferric bromide complexed with ethylene glycol or an oligoethylene glycol selected from the group consisting of di-, tri-, and tetraethylene glycol.

However, although the polyurethane materials of Chen et al and Wilson et al possess volume resistivity in a range compatible with or critical to optimal toner image transfer, they are deficient in that they both exhibit or possess relatively short electrical lives. That is, after certain hours of continuous use in an electrostatographic copying device, a biasable transfer member utilizing a polyurethane material of either Chen et al or Wilson et al must be removed from the copying device or machine and replaced with a new biasable transfer member because the original biasable transfer member no longer is capable of transferring a complete toner image from the photoconductor to the final support material (e.g. a sheet of paper). This is believed to be due to the following phenomena. Under normal operating conditions, it is necessary in order to achieve optimal image transfer to maintain a relatively constant current flow of less than about 30 micro amps in the nip area between the transfer roll surface, the transfer material and the photoconductive surface from which a developed image is to be transferred. For this condition to exist, the resistivity of the polyurethane material must be within critical values, i.e., from about $1.0\times10^6$ to about $5.0\times10^{11}$ ohm cm, as previously mentioned, and must be relatively constant under normally anticipated extremes of operating conditions. The electrical life, and hence the functional life of the biasable transfer member (i.e., the working life of the biasable transfer member) is directly related to the maintenance of this constant controlled resistivity region. That is, the electrical life of the biasable transfer member is largely determined by the stability of the output current and/or voltage versus time. (Bias roll power supplies are generally constant current or constant voltage devices with upper current or voltage limits, which respond to changes in the resistivity of the biasable, roll material, i.e., the polyurethane). Thus, as used herein, the term "electrical life" refers to a controlled, i.e., constant resistivity with time under an applied electrical field. Changes in the resistivity of the polyurethane material versus time are reflected in voltage demands required to maintain the constant current output of the material of which the device is made. As transfer current flows through the biased transfer member or roll, however, over time the ionic conductivity control additives in the polyurethane materials used in the biasable transfer roll migrate, depleting ions and increasing the resistivity of the material causing the bias voltage to increase while maintaining a constant transfer current. Eventually, substantially all of the ions are depleted and the upper voltage limit is reached beyond which point the efficient transfer of toner can no longer take place resulting in incomplete toner transfer causing undesirable side effects such as mottle or no toner transfer at all. Thus, the material used in the fabrication of a typical biasable transfer member (e.g., a biasable transfer roll) has an intrinsic electrical life directly related to the ionic depletion of the conductivity control agent in the polyurethane material. Stated another way, the problem associated with bias roll transfer systems is that the electrical life of the bias transfer member is inversely proportional to the transfer current therethrough.

Vreeland et al, in U.S. Pat. No. 5,571,457, disclose as coating materials for biasable transfer members, certain elastomeric polyurethanes containing, as conductivity control agent, a blend composed of a dicarboxylate salt of Chen et al with a ferric halide/ethylene glycol or oligoethylene glycol complex of Wilson et al in various molar ratios. According to this patent, the incorporation of the blend into a polyurethane material provides a resistivity to the polymeric material of from about $1.0 \times 10^6$ to about $5.0 \times 10^{11}$ ohm cm and in addition to that, improves or extends the electrical life of the polyurethane material beyond the electrical life of either of the polyurethane materials of Chen et al or Wilson et al. However, this patent does not mention any correlation between the electrical life and the environment in which the test was conducted.

It would be important in the art for a biasable transfer member to not only have a controlled or adjusted specific resistivity range and a constant resistivity with time under an applied electrical field but also that the resistivity and the resistivity versus time both be insensitive to widely varying changes in absolute humidity encountered in normal operating conditions such that the resistivity remains relatively constant within the range required for optimal image transfer. The present invention provides a biasable transfer member and methods for making same which has an improved or extended electrical life in dry environment compared with materials described in prior art.

SUMMARY OF THE INVENTION

The present invention describes a conductivity control agent incorporated into a polymeric material. The conductivity control agent comprises hydroxyalkylphosphonium arylsulfonate salt represented by the formula:

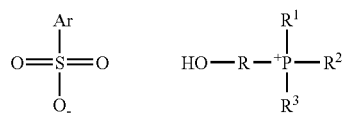

Where Ar is a substituted or unsubstituted aryl group such as phenyl, 4-methylphenyl, 3,5-bis (carbomethoxy)phenyl, 1-naphthyl, 2-naphthyl, 4-chlorophenyl, 4-nitrophenyl, 3-nitrophenyl, 4-t-butylphenyl, 4-methoxyphenyl, 2,4,6-trimethylphenyl, 2,3,4,5,6-hexafluorophenyl and the like.

R is a substituted or unsubstituted divalent alkylene moiety such as 1,2-ethylene, 1,3-propylene, 1,10-decamethylene, 2,2-dimethyl-1,3-propylene, 2-methyl-1,3-propylene, 1,2-propylene, and the like.

$R^1$, $R^2$ and $R^3$ are substituted or unsubstituted alkyl or aryl group which may be the same or different such as phenyl, 4-methylphenyl, 2,4,6-trimethylphenyl, 2,4,6-trimethoxyphenyl, 2,3,4,5,6-pentafluorophenyl, methyl, ethyl, propyl, butyl, isopropyl, cyclohexyl, t-butyl, octyl and the like.

The present invention also provides member for electrically cooperating with a conductive support surface to attract charged toner particles from the support surface towards the member which comprises a conductive substrate for supporting a uniform potential thereon and at least one layer which comprises a polymeric material having incorporated therein in an amount sufficient to provide the polymeric material with a resistivity of from about $10^6$ to about $5.0 \times 10^{11}$ ohm cm a conductivity control agent from 0.001 to 5.000 weight percent, based on the total weight of the polymeric material, the conductivity control agent comprising hydroxyalkylphosphonium arylsulfonate salt described above.

DETAILED DESCRIPTION OF THE INVENTION

Figure 1A:
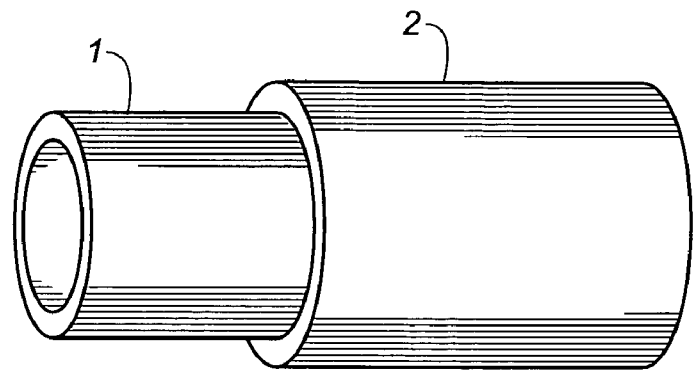
FIG. 1A is a view in partial section showing the construction of a bias transfer roll or sleeve.
Figure 1B:
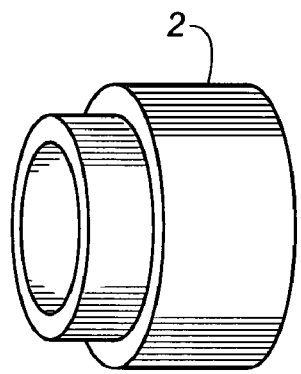
FIG. 1B is a view in partial section showing the construction of a web.
Figure 1C:
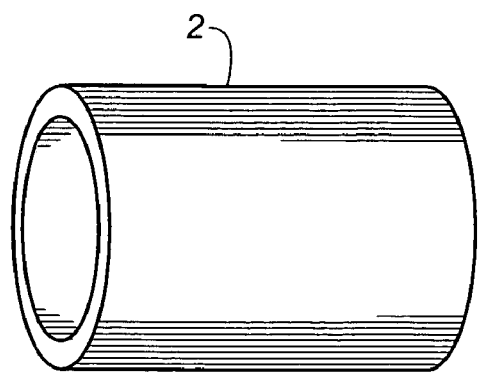
FIG. 1C is a view in partial section showing the construction of a bias transfer roll or sleeve without the conductive substrate.

By the use of the term "bias transfer member" is meant a member for electrically cooperating with a conductive support surface to attract electrically charged particles from the support surface towards the member. The transfer member could be in a form of a roll, a web or the like with or without the conductive substrate. In particular, a bias transfer roll is one, which electrically cooperates with a photoconductive plate or photoconductor, when brought into contact therewith, to attract charged toner particles from the plate or photoconductor in the direction of the roll. In this manner, the developed images are transferred from the photoconductor to a final support material, such as paper or the like. Transfer is often accomplished by wrapping the receiver around an electrically biasable transfer member and sequentially transferring the separations, in register, to the receiver by applying an appropriate electrical bias to the transfer member. Under certain circumstances, it is advantageous to transfer the toned image first to an intermediate transfer member and then from that intermediate transfer member to the receiver as disclosed by Rimai et al in U.S. Pat. No. 5,084,735 wherein the electrostatic transfer of toned images is enhanced when a compliant intermediate is used. By transferring the toned color image to the intermediate, the receiver need not be picked up and wrapped around the transfer member and then released after transfer. This allows the use of a straight paper path, which simplifies the process, and reduces the probability of having a paper jam.

Important advantages of the polyurethane coating layers of the biasable transfer members of the invention are that they possess the capability to retain a pre-established level of resistivity during electrical aging performed in dry environments.

The bias transfer members of the present invention have application in any suitable electrostatographic device such as, for example, an electrophotographic device, in which a transfer member, more particularly, a bias transfer member, is used for electrically cooperating with a photoconductive element, plate or surface when brought into contact therewith to attract toner particles bearing an electrostatic charge on the element or plate toward the transfer member. Transfer is accomplished, as in the prior art, by feeding a sheet of transfer material into the nip region formed by the surface of the transfer member and the surface of a photoconductive insulating material or element bearing a developed image and imposing a potential on the transfer member sufficient to cause the transfer of the toner particles or material from the surface of the photoconductive insulating material or element to the adjacent surface of the transfer material. In practice, any source of electrical power connected to the central conductive core of the transfer member and capable of placing the transfer member at a potential sufficient to attract toner images from the photoconductive insulating surface toward the transfer member may be employed. A more complete discussion of the principles and configurations involved in bias transfer member may be found in U.S. Pat. Nos. 2,951,443; 3,620,616; 3,633,543; 3,781,105; or 3,708,482. When an intermediate transfer member is used, the toned images are first transferred to an intermediate transfer member and then from that intermediate transfer member to the receiver. A more complete discussion of the principles and configurations involved in intermediate transfer may be found in U.S. Pat. Nos. 5,084,735; 4,737,433 or 5,370,961.

Referring specifically to FIG. 1A, there is shown a cut-away view of a transfer member illustrating the internal construction thereof. The transfer member is in the form of a roll and is basically formed upon a rigid hollow cylinder 1 that is fabricated of a conductive metal, such as aluminum, nickel, copper or the like, capable of readily responding to a biasing potential placed thereon. Over core 1 is placed a layer 2, which is a crosslinked or non-crosslinked elastomeric polyurethane containing a conductivity control agent capable of altering or controlling the resistivity of the polyurethane to within a preferred resistivity range consistent with optimal image transfer. The dimensions of the conductive roller are dictated by the design of the copy equipment into which the rollers of belts are to be incorporated.

Outer layer 2 which is formed of the resilient elastomeric material can be designed to have a hardness of between about 10 Shore A to about 80 Shore D, and preferably about 15-100 Shore A and may be about 0.040 inch (0.102 cm) to about 0.625 inch (1.58 cm) in thickness, having sufficient resiliency to allow the roll to deform when brought into moving contact with a photoconductive drum (or web) surface to provide an extended contact region in which the toner particles can be transferred between the contacting bodies. The elastomeric polyurethane coating should be capable of responding rapidly to the biasing potential to impart electrically the charge potential on the core to the outer extremities of the roll surface. It is preferred that the polyurethane layer have a resistivity of from about $1.0 \times 10^6$ to about $5.0 \times 10^{11}$ ohm cm, and, more preferably, from about $2.0 \times 10^8$ to about $2.0 \times 10^{10}$ ohm cm, as this has been found to be most consistent with optimal image transfer. This is achieved by including in the crosslinked or non-crosslinked polymeric network of the polyurethane elastomer, the conductivity control agent of the present invention. As a result, a permanent, or at the very least, a relatively constant degree of resistivity is imparted to the polyurethane elastomer that will not change substantially over time during the course of normal operations. In accordance with the present invention, the layer on the conductive substrate must be formulated of at least one layer of an elastomeric polyurethane having a conductivity control agent capable of altering and/or controlling the resistivity of the elastomer to within the preferred or desired resistivity range. By having the biasable transfer member with these particular polyurethane elastomers containing the conductivity control agents of the invention, the resistivity of the biasable transfer member is controlled and, in addition, the sensitivity of the resistivity versus time of the biasable transfer member also is minimized in relationship to changes in absolute humidity. Thus, the resistivity versus time of the elastomeric polyurethanes having conductivity control agents to control the resistivity of the polyurethanes used as the outer layer of the bias transfer member of FIG. 1A is less sensitive to electrical aging when the electrical aging is performed in low absolute humidity environments than the same elastomeric polyurethanes which are not treated with such agents. Examples of the elastomeric crosslinked or non-crosslinked polyurethane materials having conductivity control agents included in the crosslinked or non-crosslinked polymeric networks thereof as an integral part of the polyurethane material in the manner described in accordance with the invention to control the resistivity of the elastomer and hence the biasable transfer member are set forth below.

The polyurethane elastomers which can be used in accordance with the present invention are known polyurethane elastomers which are made from known starting materials using methods which are well known in the art for making polyurethane elastomers plus the conductivity control agents described herein. The conductivity control agents comprise certain products derived from the transesterification of dialkyl phosphonium 5-sulfoisophthalate salts with poly (alkylene glycols) to impart conductivity to the elastomers.

The polyurethane elastomers are the chemical reaction products of (a) polyisocyanate prepolymers formed from an isocyanate (specifically a saturated aliphatic polyisocyanate, a saturated cycloaliphatic polyisocyanate compound, or an aromatic polyisocyanate compound) reacted with a polyol, and (b), a hardener composition comprising a polyol, as previously described, or a polyamine, or a mixture thereof and an amount of the conductivity control agent described hereinbefore sufficient to control the resistivity of the polyurethane elastomer to within a range of from about $1.0 \times 10^6$ to about $5.0 \times 10^{11}$ ohm cm, and more preferably, from about $2.0 \times 10^8$ to about $2.0 \times 10^{10}$ ohm cm. The polyurethane elastomers can be crosslinked or non-crosslinked. If a crosslinked or branched polyurethane is desired, such an elastomer readily can be formed by using an excess of polyisocyanate compound in preparing the elastomer or by utilizing a polyisocyanate, a polyol and/or a polyamine having a functionality greater than two in preparing the elastomer.

The polyisocyanate prepolymer can comprise recurring units derived from any suitable polyol, including for example, amine-based polyols, polyether polyols, polyester polyols, mixtures thereof, and aromatic as well as saturated aliphatic and saturated cycloaliphatic polyisocyanates provided they do not adversely affect or in any way interfere with the humidity sensitivity or with the resistivity of the polyurethane in general. Exemplary polyisocyanate compounds, which may be used to make the prepolymer, are exemplified by those disclosed in U.S. Pat. Nos. 2,969,386 and 4,476,292, such as 4,4'-methylenediphenylene diisocyanate; 1,5-naphthalene diisocyanate; 3-isocyanatomethyl 3,5,5-trimethylcyclohexyl isocyanate (isophorone diisocyanate); methylenebis(4-isocyanatocyclohexane); hexamethylene diisocyanate; 1,3 cyclohexane bis(methylisocyanate); 2,2,4-trimethylhexamethylene diisocyanate; toluene diisocyanate and combinations thereof as well as related saturated aliphatic, saturated cycloaliphatic and aromatic polyisocyanates which may be substituted with other organic or inorganic groups that do not adversely affect the course of the polymerization reaction or interfere with the humidity sensitivity or with the resistivity of the polyurethane in general.

The term "aliphatic", as used herein includes those carbon chains, which are substantially non-aromatic in nature. They may be unbranched, branched or cyclic in configuration and may contain various substituents. Exemplary of long chain aliphatic polyisocyanates are dodecane diisocyanate, tridecane diisocyanate, and the like.

The term "aromatic" as used herein, includes a diatropic moiety derived from benzene, naphthalene, anthracene, phenanthrene, biphenyl and the like. They may be unsubstituted or substituted, for example, with halo, nitro, alkyl, alkoxy, alkylthio or aryl substituents. Included in this definition also are alkylene diarylene structures, for example, methylenediphenylene and ethylenediphenylene. Exemplary of aromatic diisocyanates are toluene-2,4-diisocyanate, m-phenylene diisocyanate, methylene-di-p-phenylene diisocyanate and the like.

Polyisocyanates as described above are commercially available. Examples of such commercially available polyisocyanate include Vibrathane B635™, which is a reaction product of a polyether with diphenylmethane diisocyanate available from Crompton Corporation.

Polyols useful in preparing the polyisocyanate prepolymer and finished polyurethane elastomers are, as previously described, any suitable polyol which will not interfere with the humidity sensitivity or with the resistivity of the polyurethane composition or otherwise adversely affect the properties and/or the performance of the polyurethane elastomer in effecting optimal image transfer of the biasable member on which the polyurethane is attached to and can include, for example, amine-based polyols, polyether polyols, polyester polyols and mixtures thereof. Examples of such polyols are disclosed in U.S. Pat. Nos. 2,969,386; 3,455,855; 4,476,292 and 4,390,679. One preferred group of polyols are aliphatic polyols and glycols such as glycerol, trimethylolpropane, 1,3-butylene glycol, 1,4-butylene glycol, 1,2-propylene glycol, 1,3-propylene glycol, hydroxylated castor oils, polyethers such as poly(tetramethylene glycols) and poly(propylene glycols), low molecular weight polyester polyols, such as polyethylene adipate, and a poly(caprolactone) diol.

A particularly useful polyol which can be used to prepare the polyisocyanate prepolymer and/or chain extend the prepolymer to the final conductive bulk polyurethane is an alkylene glycol polymer having an alkylene unit composed of at least two carbon atoms, preferably 2 to 8 carbon atoms. These alkylene glycol polymers are exemplified by poly(ethylene glycol), poly(propylene glycol) and poly(tetramethylene glycol). Di-, tri-, and tetrafunctional compounds are available with the trifunctional ones being exemplified by the reaction product of glycerol or trimethylolpropane and propylene oxide. A typical polyether polyol is available from E.I. DuPont de Nemours Company under the designation Terathane™. Also, another polyether polyol suitable for use in preparing the polyurethane materials of the present invention is a trimethylolpropane based polyfunctional polyol available from Perstorp Specialty Chemicals as TP-30™.

Another group of polyols are amine-based polyols. A wide variety of aromatic and aliphatic diamines may form part of the amine-based polyols. Such polyols include N,N,N'N'-tetrakis(2-hydroxypropyl)ethylenediamine and a polymer of ethylene diamine, propylene oxide and ethylene oxide. A typical aromatic amine-based polyol is available from Huntsman Polyurethane under the designation A-350; a typical aliphatic amine-based polyol is available from Huntsman Polyurethane under the designation A-480 and a typical ethylene diamine/propylene oxide/ethylene oxide polymer is available from BASF under the designation PLURACOL 355.

In general, suitable polyols useful for preparing the prepolymer and/or chain extending the prepolymer to the final conductive bulk polyurethane will have molecular weights of from about 60 to 10,000, typically, from about 500 to 3,000.

Preferred concentration ranges for the respective components of the prepolymer are 5-40% by weight of polyisocyanate and 60-95% by weight polyol, based on the total weight of the prepolymer, to form a resin prepolymer.

The final conductive bulk polyurethane elastomer is produced by chain extending and/or crosslinking the prepolymer with a hardener composition comprising at least one additional polyol or blends of polyols of the type aforedescribed and discussed hereinabove and the conductivity control agents described hereinbefore.

The polyol hardener system comprises at least one polyol of the type aforedescribed, such as, for example, an amine-based polyol or a polyether polyol previously identified and defined hereinabove or blends of these polyols.

Preferred polyols are poly(tetramethylene glycol) available from E.I. DuPont de Nemours Company as Terathane™ and a trimethylolpropane based polyfunctional polyol available from Perstorp Specialty Chemicals as TP-30™, having added thereto about 0.001 to about 5.000 weight percent, based on the total weight of the polyurethane elastomer, of an ionic conductivity control agent as described hereinbefore.

Alternatively, in lieu of, or in addition to, utilizing a polyol of the type and kind described hereinabove in the hardener compositions used to form the presently described polyurethane elastomers, an aliphatic or cycloaliphatic polyamine or an aromatic polyamine can be used in the hardener composition provided they do not interfere with the relative humidity sensitivity or with the resistivity of the polyurethane elastomer composition or otherwise adversely affect the properties and/or the performance of the polyurethane elastomer in effecting optimal image transfer of the biasable member on which the polyurethane is coated along with the conductivity control agents described heretofore. Exemplary diamines which can be used in the hardener compositions of the present invention include 4,4'-methylenebis(o-chloroaniline), phenylenediamine, bis(4-aminocyclohexyl)methane, isophoronyldiamine, and the reaction products of anhydrides with such polyamines as described in U.S. Pat. No. 4,390,679. Especially useful diamines are 4,4'-methylenebis(o-chloroaniline), diethyltoluenediamine available commercially from Albemarle Corporation under the trade name Ethacure 100 and di(methylthio)-2,4-toluenediamine, also available commercially from Albemarle Corporation under the trade-name Ethacure 300.

Such polyamines serve to chain extend the prepolymer to the final conductive bulk polyurethane. Suitable such polyamines will typically have molecular weights ranging from about 60 to about 500, and are employed in the hardener compositions alone having added thereto from about 0.001 to about 5.000 weight percent based on the total weight of the polyurethane of a conductivity control agent described hereinabove or as a blend in combination with one or more of the aforedescribed polyol components in weight ratios of polyamine to polyol ranging from 1:1 to 1:10 having added thereto from about 0.001 to about 5.0 weight percent based on the total weight of the polyurethane of a conductivity control agent aforedescribed.

The polyurethanes are prepared by mixing the prepolymer with the polyol or polyamine hardener.

In general, if the hardener contains stoichiometric equivalents of functional groups less than that contained in the prepolymer, a branched or crosslinked polyurethane elastomer will result. On the other hand, if the hardener contains stoichiometric equivalents of functional groups greater than or equivalent to that contained in the prepolymer, then a non-crosslinked polyurethane elastomer will result. This only applies, however, if all the components in the prepolymer and the hardener are difunctional. If any component, either in the hardener composition or in the prepolymer composition has a functionality greater than two, then the resultant polyurethane elastomer will be branched or crosslinked.

Further, and if desired, instead of preparing the polyurethane elastomers of the present invention by first forming a polyisocyanate prepolymer and hardening mixture and then reacting the two together, all of the starting materials required to form the polyurethane elastomers of the present invention may simply be added together, reacted and cured in a "one-shot" method of preparation. Or, still further, the conductivity control agents described hereinabove may be added to the polyisocyanate prepolymer instead of the hardener and the prepolymer containing the conductivity control agent and the hardener reacted together to form the polyurethane elastomers of the present invention. If either of these two methods of preparation are used, amounts of conductivity control agent in the range of from about 0.001 to about 5.000 weight percent, based on the total weight of the resultant polyurethane, generally will be appropriate for adjusting the resistivity of the polymer elastomer to within the desired limits.

Optional additives or addenda which may be included in the hardener composition may comprise, for example, ethyl acrylate-2-ethylhexyl acrylate copolymer, dimethyl siloxane copolymers and other silicones such as SAG-47 commercially available from Union Carbide Company; antioxidants, such as esters of β-(3,5-di-tert-butyl-4-hydroxyphenyl) propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris(hydroxyethyl)isocyanurate, and di(hydroxyethyl)oxalic acid diamide; UV absorbers and light stabilizers such as 2-(2'-hydroxyphenyl)benzyltriazoles and sterically hindered amines such as bis(2,2,6,6-tetramethylpiperidyl)sebacate, bis(1,2,2,6,6-pentamethylpiperidyl)sebacate, n-butyl-3,5-di-tert-butyl-4-hydroxybenzyl malonic acid, bis(1,2,2,6,6-pentamethylpiperidyl)ester, condensation product of 1-hydroxyethyl-2,2,6,6-tetramethyl-4-hydroxypiperidine and succinic acid, condensation product of N,N'-bis (2,2,6,6-tetramethylpiperidyl)hexamethylenediamine, and 4-tert-octylamino-2,6-dichloro-1,3,5-s-triazine, tris(2,2,6,6-tetramethylpiperidyl)nitrilotriacetate, tetrakis (2,2,6,6-tetramethyl-4-piperidyl)-1,2,3,4-butanetetracarbonic acid and 1,1'-(1,2-ethanediyl)-bis-(3,3,5,5-tetramethylpiperazinone); plasticizers such as phthalates, adipates, glutarates, epoxidized vegetable oils, and the like; fungicides, pigments, dyes; reactive dyes; moisture scavengers; and the like.

Catalysts are known to those skilled in the art and may be used to speed up the rate of the polymerization. Typical catalysts include organo-metallic catalyst such as dibutyltin dilaurate and tertiary amine such as Dabco (1,4-diazabicyclo [2.2.2]octane).

Generally stoichiometric amounts of prepolymer and polyols are utilized, with the possibility of deviating from the stoichiometric amount by utilizing excess of prepolymer or polyol.

The prepolymer-hardener mixtures prior to curing, exhibit sufficiently low viscosities to facilitate mixing, pouring and air bubble diffusion, thereby allowing for the formation of bubble free castings in the configuration of a transfer member.

Two-component polyurethane mixes of the type described above into which the conductivity control agents of the invention can be incorporated are commercially available. Examples of such commercially available polyurethane systems include CONATHANE TU-8040 and CONATHANE TU-8050 available from Conap Inc., Olean, N.Y.

The degree of conductivity imparted to the polymer will vary depending primarily upon the amount of conductivity control agent included in the combination of starting materials and the inherent properties of the given polymer and crosslinking agent, if employed, (i.e., the degree of conductivity the polymer would have if no conductivity control agent were included). Any amount of the conductivity control agent sufficient to adjust or alter the resistivity of the elastomeric polyurethane material to within the desired limits, e.g., from higher levels of resistivity to a resistivity in the range of from about $1.0 \times 10^6$ to about $5.0 \times 10^{11}$ ohm cm, may be used in accordance with the present invention. Resistivity in this range has been found to be consistent with optimal image transfer efficiency. In general, as mentioned previously, concentrations in the range of about 0.001 to 5.000 percent by weight, based on the total weight of the elastomeric polyurethane, have been found to be appropriate for adjusting the resistivity of the polymer to within the desired limits.

Higher amounts of the conductivity control agent may be used, however, to control the resistivity of the polyurethane elastomer, the only limitation being that the elastomeric polyurethane used as the a layer on the conductive substrate of the biasable transfer member possess the desired resistivity.

The conductivity control agent is simply included in the desired amount in the combination of starting materials, typically, but not necessarily, as a component of the hardener composition. The conductivity control agent will bond covalently to the polymer matrix, i.e., to the backbone and/or a crosslinking, and/or a branched portion of the polymer by reaction of the hydroxyl group, for example, with excess isocyanate present in the prepolymer/hardener mixtures which form urethane linkages in the polymer backbone and/or crosslinking and/or branched portions of the polymer during the normal process of elastomer preparation thereby firmly anchoring the conductivity control agent in the polymeric network.

The conductivity control agents which are incorporated into the polyurethane elastomers in accordance with the present invention for controlling or adjusting the resistivity of the polyurethane and for reducing the sensitivity of the resistivity of the polyurethane elastomers to changes in humidity are those salts represented by the formula:

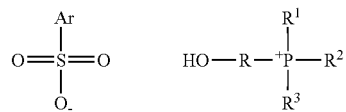

Where Ar =a substituted or unsubstituted aryl group such as phenyl, 4-methylphenyl, 3,5-bis(carbomethoxy)phenyl, 1-naphthyl, 2-naphthyl, 4-chlorophenyl, 4-nitrophenyl, 3-nitrophenyl, 4-t-butylphenyl, 4-methoxyphenyl, 2,4,6-trimethylphenyl, 2,3,4,5,6-hexafluorophenyl and the like.

R=a substituted or unsubstituted divalent alkylene moiety such as 1,2-ethylene, 1,3-propylene, 1,10-decamethylene, 2,2-dimethyl-1,3-propylene, 2-methyl-1,3-propylene, 1,2-propylene, and the like.

R1, R2 and R3=substituted or unsubstituted alkyl or aryl group which may be the same or different such as phenyl, 4-methylphenyl, 2,4,6-trimethylphenyl, 2,4,6-trimethoxyphenyl, 2,3,4,5,6-pentafluorophenyl, methyl, ethyl, propyl, butyl, isopropyl, cyclohexyl, t-butyl, octyl and the like.

Specific examples of salts useful in the practice of the present invention include, but are not limited to the following:

(2-Hydroxyethyl)triphenylphosphonium 3,5-bis(carbomethoxy)benzenesulfonate

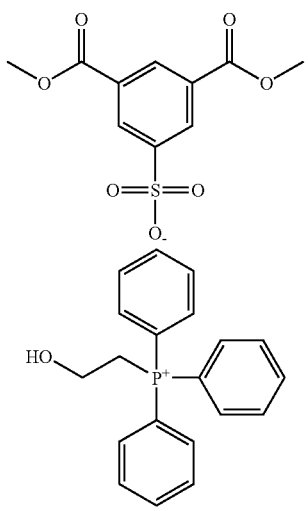

(2-Hydroxyethyl)tributylphosphonium 3,5-bis(carbomethoxy)benzenesulfonate

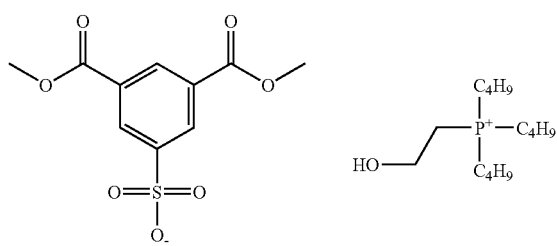

(2-Hydroxyethyl)triphylphosphonium 4-methylbenzenesulfonate

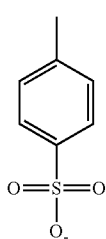 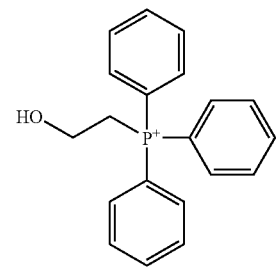

(3-Hydroxypropyl)triphenylphosphonium 3,5-bis(carbomethoxy)benzenesulfonate

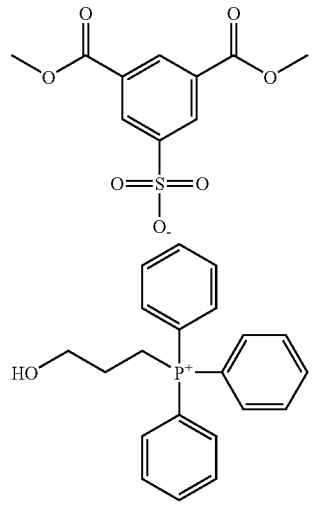

The hydroxyalkylphosphonium arylsulfonate salts used as conductivity control agents in the practice of the invention can be prepared from an appropriate arylsulfonate salt and an appropriate hydroxyalkylphosphonium halide by a metathesis reaction.

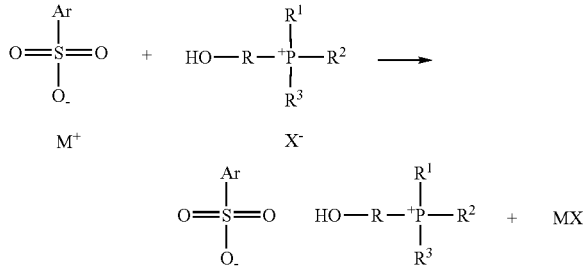

Alternatively, the hydroxyalkylphosphonium arylsulfonate salts of the invention may also be prepared by the alkylation of a tertiary phosphine with a hydroxyalkyl arylsulfonate.

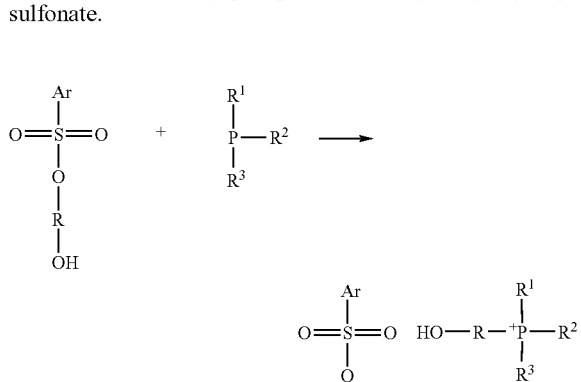

The hardness of the electrically conductive or semi-conductive elastomeric polyurethanes of the invention, when used as a layer material in a biasable transfer member, is between about 10 Shore A to about 80 Shore D, and preferably about 15-100 Shore A. The control of the hardness is within the purview of those skilled in the art and the hardness can be controlled by such parameters as by varying the types and amounts of reactants used and by using various additives such as plasticizers.

The layer can be applied to the substrate by any suitable method or technique known in the art including spraying, casting in molds, affixing sheets of the material to the substrate member by suitable mechanical means or by suitable cement, and the like.

The biasable transfer members of the present invention have application in any suitable electrostatographic device such as, for example, an electrophotographic device, in which a transfer member, more particularly, a bias transfer member, is used for electrically cooperating with a photoconductive element, plate or surface when brought into contact therewith to attract toner particles bearing an electrostatic charge on the element or plate toward the transfer member. Transfer is accomplished, as in the prior art, by feeding a sheet of transfer material into the nip region formed by the surface of the transfer member and the surface of a photoconductive insulating material or element bearing a developed image and imposing a potential on the transfer member sufficient to cause the transfer of the toner particles or material from the surface of the photoconductive insulating material or element to the adjacent surface of the transfer material. If the biasable transfer member is to be used as an intermediate transfer member the toned images will be transferred first to an intermediate transfer member and then from that intermediate transfer member to the receiver.

The following examples and comparative tests illustrate more clearly the elastomeric polyurethane materials of the present invention which may be used in the fabrication of the biasable transfer members as discussed above and for controlling the resistivity and extending the electrical life of the biasable transfer member, including controlling the sensitivity of the resistivity of the member to changes in humidity although the invention is not to be construed as limited in scope thereby.

Although it is not understood at the present time why the conductivity control agents of the present invention when incorporated into a polymeric material of the type disclosed herein extend or improve the electrical life of the polymeric material, it is evident that these conductivity control agents are able to maintain a constant transfer current passing through the polymeric material for a period of time exceeding both that of the additives of Chen et al or Wilson et al when the material is electrically aged in a low humidity environment.

As mentioned previously, the conductivity control agents used in the present invention for controlling or adjusting the resistivity of the polyurethane elastomers which form the coatings on the conductive substrate of the biasable transfer members of the invention significantly reduce the electrical aging of the material by minimizing the resistivity versus time variation of a sample being aged in a low humidity environment.

Sample Preparation:

Buttons of a particular elastomeric polyurethane to be tested were cast in a stainless steel mold to a thickness of 0.5 in (1.27 cm) and an outside diameter of 2 in (5.08 cm). The samples of various compositions were placed in controlled humidity chambers for a selected number of days. One chamber was maintained at 70° F. and relative humidity of 50% and another chamber was maintained at 70° F. and relative humidity of 20%. The samples were suspended in the chambers in such a way that both sides were exposed to the atmospheric conditions. By this procedure, the samples would have been very close to the equilibrium amounts of water within 14 days. After the samples reached the equilibrium, initial resistivity measurements of fresh samples and electrical aging tests were carried out. The initial resistivity was measured both at 20 percent relative humidity (2.6 $g/m^3$ absolute humidity) and 50 percent relative humidity (17.5 $g/m^3$ absolute humidity). For the designated examples below, before electrical aging (fresh), the ratio of the resistivity at 2.6 $g/m^3$ absolute humidity to the resistivity at 17.5 $g/m^3$ absolute humidity was determined. The resulting ratio was designated as the absolute humidity sensitivity or absolute humidity swing and is reported as absolute humidity sensitivity in Table I below where resistivities at 2.6 $g/m^3$ and 17.5 $g/m^3$ absolute humidities also are designated for the various samples tested. The electrical aging tests consisted of placing samples between two electrodes having a cross section area of 3.14 $in^2$ (20.27 $cm^2$). A constant current of 30 µamps was applied to one electrode and the other electrode was ground. Current flow through the sample was monitored via the voltage drop across the load resistor. The voltage drop was sent to a computer data acquisition system with a sample rate of 15 minutes. Aging of the slabs was conducted for 50 hours. Electrical aging of the samples was measured by dividing the final volume resistivity of the buttons by the initial volume resistivity of the buttons to determine the increase in volume resistivity over time between the initial volume resistivity and final volume resistivity. The smallest increase in volume resistivity was representative of the button possessing the longest electrical life.

EXAMPLE 1

This example describes the preparation of a conductivity control agent useful in accordance with the invention, which is (2-hydroxyethyl)triphenylphosphonium 3,5-bis(carbomethoxy)benzenesulfonate salt.

To a hot solution of 11.85g (40 mmol) of dimethyl 5-sodiosulfoisphthalate in 80 ml of water was added a hot solution of 15.49g (40 mmol) of (2-hydroxyethyl)triphenylphosphonium bromide in 80 ml of water. A precipitate immediately formed which was cooled, collected and washed with water. The crude material was recrystallized from 2-butanone, collected and dried.

The NMR spectrum ($CDCl_3$) was consistent with the proposed structure.

Examples 2 and 3 describe the preparation of elastomeric polyurethane containing, as an additive, the conductivity control agent of the present invention, (2-hydroxyethyl)triphenylphosphonium 3,5-bis(carbomethoxy)benzenesulfonate salt, at two concentrations, which correspond to 0.2 wt % of the total polyurethane weight and 0.5 wt % of the total polyurethane weight, respectively.

EXAMPLE 2

This example describes the preparation of a crosslinked 50 Durometer Shore A hardness elastomeric polyurethane containing, as an additive, the conductivity control agent of the present invention, (2-hydroxyethyl)triphenylphosphonium 3,5-bis(carbomethoxy)benzenesulfonate salt prepared according to Example 1.

To a one-liter plastic beaker containing 95.832 g (193.765 meq) of Terathane 1000, a poly(tetramethylene glycol) available from E.I. DuPont de Nemours Company, 0.5 g (0.861 meq) (2-hydroxyethyl)triphenylphosphonium 3,5-bis(carbomethoxy)benzenesulfonate salt and 3 drops of a polydimethylsiloxane anti-foam agent obtained from Union Carbide under the trade name of SAG 47, were added 7.260 g (77.506 meq) of ethoxylated trimethylolpropane obtained commercially from Perstorp Specialty Chemicals under the trade name of polyol TP 30. The mixture was stirred and next, 146.407 g (272.133 meq) of a polyether-based polyurethane prepolymer obtained from Crompton Corporation as Vibrathane B635™, a diphenylmethane diisocyanate/polyether prepolymer were added. The reaction mixture was stirred at room temperature for two minutes degassed under reduced pressure (0.1 mm Hg) and poured into stainless steel molds. The polymer was cured at 100° C. for sixteen hours and demolded. The buttons were then cooled to room temperature and put in a controlled chamber for fourteen days for equilibration prior to the electrical aging test. The initial resistivity of non-aged samples was measured as described above at the two designated absolute humidities and the absolute humidity sensitivity was determined after an equilibration time of fourteen days. The results are shown in Table I below.

EXAMPLE 3

This example describes the preparation of a crosslinked 50 Durometer Shore A hardness elastomeric polyurethane containing, as an additive, the conductivity control agent of the present invention, (2-hydroxyethyl)triphenylphosphonium 3,5-bis(carbomethoxy)benzenesulfonate salt prepared according to example 1.

To a one-liter plastic beaker containing 95.276 g (192.641 meq) of Terathane 1000, a poly(tetramethylene glycol) available from E.I. DuPont de Nemours Company, 1.250 g (2.153 meq) (2-hydroxyethyl)triphenylphosphonium 3,5-bis(carbomethoxy)benzenesulfonate salt and 3 drops of a polydimethylsiloxane anti-foam agent obtained from Union Carbide under the trade name of SAG 47, were added 7.218 g (77.056 meq) of ethoxylated trimethylolpropane obtained commercially from Perstorp Specialty Chemicals under the trade name of polyol TP 30. The mixture was stirred and next, 146.256 g (271.851 meq) of a polyether-based polyurethane prepolymer obtained from Crompton Corporation as Vibrathane B635™, a diphenylmethane diisocyanate/polyether prepolymer were added. The reaction mixture was stirred at room temperature for two minutes degassed under reduced pressure (0.1 mm Hg) and poured into stainless steel molds. The polymer was cured at 100° C. for sixteen hours and demolded. The buttons were then cooled to room temperature and put in a controlled chamber for fourteen days for equilibration prior to the electrical aging test. The initial resistivity of non-aged samples was measured as described above at the two designated absolute humidities and the absolute humidity sensitivity was determined after an equilibration time of fourteen days. The results are shown in Table I below.

Comparative Examples 4 and 5 describe the preparation of elastomeric polyurethane containing, as an additive, the conductivity control agent of prior art, bis[oxydiethylenebis (polycaprolactone)yl] 5-sulfo-1,3 -benzenedicarboxylate, methyltriphenylphosphonium salt, at two concentrations, which correspond to 0.54 wt % of the total polyurethane weight and 1.25 wt % of the total polyurethane weight, respectively.

COMPARATIVE EXAMPLE 4

This describes the preparation of a crosslinked 55 Durometer Shore A hardness elastomeric polyurethane outside the scope of this invention to compare the electrical aging of the polyurethane of the present invention to the electrical aging of the polyurethane materials of the prior art, specifically those described in U.S. Pat. No. 4,729,925 to Chen et al, with respect to resistivity stability in dry environments.

To a one-liter plastic beaker containing 123.60 g (249.903 meq) of Terathane 1000, a poly(tetramethylene glycol) available form E.I. DuPont de Nemours Company, 1.620 g (1.620 meq) Bis[oxydiethylenebis(polycaprolactone)yl]5-sulfo-1, 3-benzenedicarboxylate, methyltriphenylphosphonium salt prepared in accordance with the method of Example 10 in U.S. Pat. No. 4,729,925 and 3 drops of a polydimethylsiloxane anti-foam agent obtained from Union Carbide under the trade name of SAG 47, were added 5.852 g (62.476 meq) of ethoxylated trimethylolpropane obtained commercially from Perstorp Specialty Chemicals under the trade name of polyol TP 30. The mixture was stirred and next, 168.93 g (313.998 meq) of a polyether-based polyurethane prepolymer obtained from Crompton Corporation as Vibrathane B635™, a diphenylmethane diisocyanate/polyether prepolymer were added. The reaction mixture was stirred at room temperature for two minutes degassed under reduced pressure (0. 1 mm Hg) and poured into stainless steel molds. The polymer was cured at 100° C. for sixteen hours and demolded. The buttons were then cooled to room temperature and put in a controlled chamber for fourteen days for equilibration prior to the electrical aging test. The initial resistivity of non-aged samples was measured as described above at the two designated absolute humidities and the absolute humidity sensitivity was determined after an equilibration time of fourteen days. The results are shown in Table I below.

COMPARATIVE EXAMPLE 5

This describes the preparation of a crosslinked 55 Durometer Shore A hardness elastomeric polyurethane outside the scope of this invention to compare the electrical aging of the polyurethane of the present invention to the electrical aging of the polyurethane materials of the prior art, specifically those described in U.S. Pat. No. 4,729,925 to Chen et al, with respect to resistivity stability in dry environments.

To a one-liter plastic beaker containing 122.24 g (247.151 meq) of Terathane 1000, a poly(tetramethylene glycol) available form E.I. DuPont de Nemours Company, 3.750 g (3.750 meq) Bis[oxydiethylenebis(polycaprolactone)yl]5-sulfo-1, 3-benzenedicarboxylate, methyltriphenylphosphonium salt prepared in accordance with the method of Example 10 in U.S. Pat. No. 4,729,925 and 3 drops of a polydimethylsiloxane anti-foam agent obtained from Union Carbide under the trade name of SAG 47, were added 5.788 g (61.788 meq) of ethoxylated trimethylolpropane obtained commercially from Perstorp Specialty Chemicals under the trade name of polyol TP 30. The mixture was stirred and next, 168.23 g (312.689 meq) of a polyether-based polyurethane prepolymer obtained from Crompton Corporation as Vibrathane B635™, a diphenylmethane diisocyanate/polyether prepolymer were added. The reaction mixture was stirred at room temperature for two minutes degassed under reduced pressure (0.1 mm Hg) and poured into stainless steel molds. The polymer was cured at 100° C. for sixteen hours and demolded. The buttons were then cooled to room temperature and put in a controlled chamber for fourteen days for equilibration prior to the electrical aging test. The initial resistivity of non-aged samples was measured as described above at the two designated absolute humidities and the absolute humidity sensitivity was determined after an equilibration time of fourteen days. The results are shown in Table I below.

COMPARATIVE EXAMPLE 6

This describes the preparation of a crosslinked 55 Durometer Shore A hardness elastomeric polyurethane outside the scope of this invention to compare the electrical aging of the polyurethane of the present invention to the electrical aging of the polyurethane materials of the prior art, specifically those described in U.S. Pat. No. 5,571,457 to Vreeland et al, with respect to resistivity stability in dry environments.

To a one-liter plastic beaker containing 162.44g (328.438 meq) of Terathane 1000, a poly(tetramethylene glycol) available form E.I. DuPont de Nemours Company, 4.24 g (8.840 meq) Bis[oxydiethylenebis(polycaprolactone)yl] 5-sulfo-1,3-benzenedicarboxylate, methyltriphenylphosphonium and a diethylene glycol-ferric chloride complex at a molar ratio of 1:1 prepared in accordance with the method of Example 1 in U.S. Pat. No. 5,571,457 and 3 drops of a polydimethylsoloxane anti-foam agent obtained from Union Carbide under the trade name of SAG 47, were added 7.69 g (82.109 meq) of ethoxylated trimethylolpropane obtained commercially from Perstorp Specialty Chemicals under the trade name of polyol TP 30. The mixture was stirred and next, 225.63 g (419.387 meq) of a polyether-based polyurethane prepolymer obtained from Crompton Corporation as Vibrathane B635™, a diphenylmethane diisocyanate/polyether prepolymer were added. The reaction mixture was stirred at room temperature for two minutes degassed under reduced pressure (0.1 mm Hg) and poured into stainless steel molds. The polymer was cured at 100° C. for sixteen hours and demolded. The buttons were then cooled to room temperature and put in a controlled chamber for fourteen days for equilibration prior to the electrical aging test. The initial resistivity of non-aged samples was measured as described above at the two designated absolute humidities and the absolute humidity sensitivity was determined after an equilibration time of fourteen days. The results are shown in Table I below.

TABLE I

Absolute Humidity Sensitivity After 2 Weeks Equilibration

| Polyurethane Example | volume resistivity (Ohms · cm) at 2.6 g/m$^3$ | volume resistivity (Ohms · cm) at 17.5 g/m$^3$ | Absolute humidity sensitivity |
|---|---|---|---|
| 2 | 3.39E+09 | 8.55E+08 | 3.96 |
| 3 | 1.82E+09 | 4.64E+08 | 3.92 |
| 4 | 1.99E+09 | 5.00E+08 | 3.98 |
| 5 | 1.18E+09 | 2.90E+08 | 4.07 |
| 6 | 3.36E+08 | 1.26E+08 | 2.66 |

As shown in Table I, a comparison of the absolute humidity sensitivity and resistivity of the polyurethane elastomer of examples 2 and 3 containing the (2-hydroxyethyl)triphenylphosphonium 3,5-Bis(carbomethoxy)benzenesulfonate salt conductivity control agent of the present invention and the polyurethane elastomer from example 4 and 5 of Example 10 in U.S. Pat. No. 4,729,925 to Chen et al shows similar behavior in terms of absolute humidity sensitivity of the polyurethane elastomer of the present invention compared to the prior art conductivity control agents of Chen et al in U.S. Pat. No. 4,729,925. However, the polyurethane elastomer from Example 6 of Example 1 in U.S. Pat. No. 5,571,457 to Vreeland et al shows lower absolute humidity sensitivity than the conductivity control agents of the present invention.

The main advantage of the conductivity control agents of the present invention will be exemplified in the following Example 7 where a substantial improvement in electrical aging at low humidity environment is observed for the conductivity control agent of the present invention compared with the prior art examples of Chen et al in U.S. Pat. No. 4,729,925 and Vreeland et al in U.S. Pat. No. 5,571,457.

EXAMPLE 7

Electrical aging tests were carried out using the polyurethane materials of Examples 2 through 6 to show that the polyurethane elastomers of the present invention are superior to those of the prior art, specifically those described in U.S. Pat. No. 5,571,457 to Vreeland et al and those described in U.S. Pat. No. 4,729,925 to Chen et al with respect to improved and extended electrical life.

The electrical aging tests consisted of placing samples between two electrodes having a cross section area of 3.14 in$^2$ (20.27 cm$^2$). A constant current of 30 μamps was applied to one electrode and the other electrode was ground. Current flow through the sample was monitored via the voltage drop across the load resistor. The voltage drop was sent to a computer data acquisition system with a sample rate of 15 minutes. Aging of the slabs was conducted for at least 30 hours. Electrical aging of the samples was measured by dividing the final volume resistivity of the buttons by the initial volume resistivity of the buttons to determine the increase in volume resistivity over time between the initial volume resistivity and final volume resistivity. The smallest increase in volume resistivity was representative of the button possessing the longest electrical life.

The aging device was place in a chamber that was kept at 60° F. and 20% Relative Humidity corresponding to an absolute humidity of 2.6 grams of water per m$^3$.

The results are reported in Table II, below.

TABLE II

Electrical Aging

| Samples | Initial volume resistivity (Ohms · cm) | Final volume resisitivity (Ohms · cm) | Final volume resistivity div.initial volume resistivity |
|---|---|---|---|
| 2 | 3.39E+09 | 7.02E+09 | 2.07 |
| 3 | 1.82E+09 | 3.12E+09 | 1.71 |
| 4 | 1.99E+09 | 5.52E+09 | 2.77 |
| 5 | 1.18E+09 | 3.10E+09 | 2.63 |
| 6 | 3.36E+08 | 3.31E+09 | 9.87 |

As shown in table II, the polyurethane materials of the present invention (examples 2 and 3) exhibit improved or extended electrical life as compared to the polyurethane materials of either Chen et al or Wilson et al when the materials go through an electrical aging test at low absolute humidity such as 2.6 grams of water/m$^3$.

The invention has been described in detail with particular reference to certain preferred embodiments thereof, but it will be understood that variations and modifications can be effected within the spirit and scope of the invention.

It is claimed:

1. A member for electrically cooperating with a conductive support surface to attract charged toner particles from the support surface towards the member which comprises a conductive substrate for supporting a uniform potential thereon and at least one layer which comprises a polymeric material having incorporated therein in an amount sufficient to provide the polymeric material with a resistivity of from about 10$^6$ to about 5.0×10$^{11}$ ohm cm a conductivity control agent from 0.001 to 5.000 weight percent, based on the total weight of the polymeric material, the conductivity control agent comprising a hydroxyalkylphosphonium sulfonate salt represented by the formula:

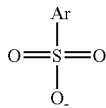 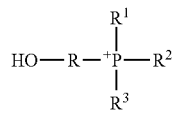

where Ar comprises a substituted or unsubstituted aryl group;

R comprises substituted or unsubstituted divalent alkylene moiety;

$R^1$, $R^2$ and $R^3$ comprises substituted or unsubstituted alkyl or aryl group which may be the same or different.

2. The member of claim 1 wherein Ar comprises phenyl, 4-methylphenyl, 3,5-bis (carbomethoxy)phenyl, 1-naphthyl, 2-naphthyl, 4-chlorophenyl, 4-nitrophenyl, 3-nitrophenyl, 4-t-butylphenyl, 4-methoxyphenyl, 2,4,6-trimethylphenyl or 2,3,4,5,6-hexafluorophenyl.

3. The member of claim 1 wherein R comprises 1,2-ethylene, 1,3-propylene, 1,10-decamethylene, 2,2-dimethyl-1,3-propylene, 2-methyl-1,3-propylene or 1,2-propylene.

4. The member of claim 1 wherein $R^1$, $R^2$ and $R^3$ comprise phenyl, 4-methylphenyl, 2,4,6-trimethylphenyl, 2,4,6-trimethoxyphenyl, 2,3,4,5,6-pentafluorophenyl, methyl, ethyl, propyl, butyl, isopropyl, cyclohexyl, t-butyl or octyl.

5. The member of claim 1 wherein the layer has a resistivity of from $2.0 \times 10^8$ to about $2.0 \times 10^{10}$ ohm-cm.

6. The member of claim 1 wherein the layer has a hardness of about 10 Shore A and 80 Shore D.

7. The member of claim 1, wherein the polymeric material is selected from the group consisting of elastomeric polymers, polyurethanes, polyurethane foams, adhesive polymers, plastics and rubbers.

8. The member of claim 1 wherein the conductive substrate comprises an endless belt.

9. The member of claim 1 wherein the conductive substrate comprises a roll.

10. The member of claim 1 wherein the conductive support surface comprises a photoconductor.

11. A method of controlling the resistivity of a member for electrically cooperating with a conductive support surface to attract charged toner particles from the surface towards the member comprising a conductive substrate for supporting a uniform potential thereon and at least one layer which comprises a polymeric material, wherein the method comprises incorporating therein in an amount sufficient to provide the polymeric material with a resistivity of from about $10^6$ to about $5.0 \times 10^{11}$ ohm cm a conductivity control agent from 0.001 to 5.000 weight percent, based on the total weight of the polymeric material, the conductivity control agent comprising a hydroxyalkylphosphonium sulfonate salt represented by the formula:

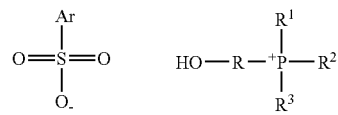

where Ar comprises a substituted or unsubstituted aryl group;

R comprises a substituted or unsubstituted divalent alkylene moiety;

$R^1$, $R^2$ and $R^3$ comprises substituted or unsubstituted alkyl or aryl group which may be the same or different.

* * * * *